(12) United States Patent
Esfandiari

(10) Patent No.: US 7,959,877 B2
(45) Date of Patent: Jun. 14, 2011

(54) IMMUNOASSAY APPARATUS AND KIT

(75) Inventor: Javanbakhsh Esfandiari, Stoney Brook, NY (US)

(73) Assignee: Chembio Diagnostic Systems, Inc., Medford, NY (US)

( * ) Notice: Subject to any disclaimer, the term of this patent is extended or adjusted under 35 U.S.C. 154(b) by 1528 days.

(21) Appl. No.: 11/317,118

(22) Filed: Dec. 22, 2005

(65) Prior Publication Data
US 2007/0148049 A1 Jun. 28, 2007

(51) Int. Cl.
B01L 3/00 (2006.01)
(52) U.S. Cl. ............... 422/530; 422/405; 422/547
(58) Field of Classification Search ............... 422/57, 422/58, 61, 99, 102, 405, 430, 547; 436/69, 436/70, 174, 175, 176, 179, 180
See application file for complete search history.

(56) References Cited

U.S. PATENT DOCUMENTS

| | | | |
|---|---|---|---|
| 4,235,601 A | 11/1980 | Deutsch et al. | |
| 4,299,916 A | 11/1981 | Litman et al. | |
| 4,409,988 A | 10/1983 | Greenspan | |
| 4,418,702 A | 12/1983 | Brown et al. | |
| 4,580,577 A | 4/1986 | O'Brien et al. | |
| 4,635,488 A | 1/1987 | Kremer | |
| 4,774,962 A | 10/1988 | Hebel et al. | |
| 4,820,399 A | 4/1989 | Senda et al. | |
| 4,900,663 A | 2/1990 | Wie et al. | |
| 4,978,504 A | 12/1990 | Nason | |
| 4,999,285 A | 3/1991 | Stiso | |
| 5,030,558 A | 7/1991 | Litman et al. | |
| 5,039,607 A | 8/1991 | Skold et al. | |
| 5,056,521 A | 10/1991 | Parsons et al. | |
| 5,141,850 A | 8/1992 | Cole et al. | |
| 5,935,864 A | 8/1999 | Schramm et al. | |
| 6,375,896 B1 * | 4/2002 | Wuske et al. | 422/58 |
| 6,634,243 B1 | 10/2003 | Wickstead et al. | |
| 6,924,498 B2 * | 8/2005 | Feldsine et al. | 250/573 |
| 7,378,054 B2 * | 5/2008 | Karmali | 422/57 |

* cited by examiner

*Primary Examiner* — Jill Warden
*Assistant Examiner* — Dwayne K Handy
(74) *Attorney, Agent, or Firm* — Gordon & Jacobson, PC

(57) ABSTRACT

Biological sampling apparatus have a barrel defining a chamber with a narrow passageway at one end and an absorbent analytical test means in the chamber. In one embodiment, an integral frit is provided with a first portion acting as a splash filter and located in the chamber, and a second portion integral with said first portion acting as a wick. The second portion extends through the narrow passageway. A portion of the splash filter is hydrophobic, and at least a portion of the wick is treated with a wetting agent and is hydrophilic. In another embodiment, a splash filter is located in the chamber and a separate hydrophilic wick is provided having a first portion located in the narrow passageway and a second portion located outside the passageway and barrel. The second portion has a bulbous portion capable of absorbing substantially more fluid sample than the first portion.

22 Claims, 3 Drawing Sheets

IMMUNOASSAY APPARATUS AND KIT

BACKGROUND OF THE INVENTION

1. Field of the Invention

This invention relates broadly to apparatus for collecting, processing and analyzing a liquid specimen. More particularly, this invention relates to an immunoassay apparatus and kit particularly useful for diagnosing disease.

2. State of the Art

Body fluid sampling and testing usually involves four steps: sample collection, extraction of the sample from the collection media, reaction of the sample with analytical reagents, and detection and/or measurement of physiologically active contents. The sampling of body fluids (e.g., blood), is typically accomplished in the field by trained personnel (e.g., nurses). The extraction of the sample, reaction of the sample with analytical reagents, and detection and/or measurement of contents has been traditionally performed in specialized laboratories by laboratory technicians. Recently, classical methods of analytical chemistry have been increasingly replaced by automated analyzers designed for the processing of well-defined specimens. These procedures are typically still conducted in highly specialized institutions by technicians trained in operating particular instruments. In addition, there has been an increasing recent trend to provide devices for the analysis of specimens in the field.

Several devices and methods have been described to collect liquid specimens by means of fibrous or other absorbent materials for subsequent processing and analysis. U.S. Pat. No. 4,409,988 to Greenspan teaches an apparatus for collecting cultures where the specimen is taken up by the absorbent tip of a swab which is then transferred into a culture medium. Similarly, U.S. Pat. No. 4,987,504 to Nason describes a specimen test unit for which the biological sample is also collected with a swab. For the collection of a specimen for medical diagnosis, EP 0 382 905 A2 to Schluter teaches the use of absorbent material for uptake of liquid and simultaneous separation of particulate matter. U.S. Pat. No. 4,635,488 to Kremer discloses a device with a nib containing porous material for absorption of a sample. A number of devices have been described for collecting oral fluid using an absorbent pad and extracting the fluid from the pad either with a barrel-piston arrangement—see, e.g., U.S. Pat. Nos. 4,418,702; 4,580,577; 4,774,962; 5,056,521, or by centrifugation—see, e.g., U.S. Pat. No. 4,774,962.

All of these applications teach the use of absorbent material to take up a liquid to be analyzed. However, each of these apparatus have certain limitations. In some cases, the absorbent material utilized has a large surface area which absorbs the sample and makes quantitative analysis difficult when the components to be analysed are in a low concentration. In other cases, the absorbent material can destroy or modify the molecules or components of the sample; e.g., via hemolysis of red blood cells in whole blood specimens, catalytic reactions, chemical reactions, etc.) In certain cases the provided absorbent material results in an inaccurate volume uptake, particularly in the situation of viscous liquids such as whole blood. In yet other cases, the absorbent material has a limited capacity for expression or desorption of the liquid taken up, so that it is difficult to recover small samples.

In an attempt to overcome these problems, U.S. Pat. No. 5,935,864 Schramm et al. which is hereby incorporated by reference herein in its entirety, provides a sample kit including a sample container with an open end and a capillary end and with a chamber disposed therebetween which includes an analytical testing strip. A reagent vial is provided with a penetrable foil seal. Liquid specimens are collected by bringing the capillary end of the sample container into contact with the liquid specimen to be analysed. The specimen is then tested by penetrating the foil seal of the reagent vial with the capillary end such that reagent is forced through the capillary end and into the chamber, thereby attempting to force contact of the sample with the analytical testing strip.

While the sample kit of Schramm et al. does overcome some of the problems of the prior art, it has its own problems. For example, the arrangement of using a reagent vial and forcing the reagent through the capillary end typically results in splashing within the chamber which results in some or all of sample not contacting the test strip. To overcome this problem, a splash filter has been utilized at the entrance of the capillary into the chamber. Another problem with the sample kit of Schramm et al. is the extremely limited amount of sample that is obtained by the capillary. Commercial product utilizing capillary action for sample take up collects approximately 3 microliters of blood. This amount of sample is not compatible with many test applications such as tuberculosis (TB) serology and TB antigen tests and other antigen detection systems which generally require larger sample volumes (e.g., 10-40 microliters). Further, problems arise with respect to the collection of blood with the Schramm et al. design because of the risk of an air bubble locating in the tip of the barrel which prevent capillary movement of the blood. Further yet, where a plasma or serum sample is to be analyzed, the sample should be provided to the capillary tip by a laboratory pipette, because the plasma or serum is often clear and successful capillary action is not readily evident to the naked eye. Dipping the barrel into the sample is not recommended because of air bubbles and the likelihood that there may not be enough back pressure to cause the sample to move up the capillary.

SUMMARY OF THE INVENTION

It is therefore an object of the invention to provide an apparatus for collecting and analyzing a fluid specimen which may be reliably used with blood, serum, saliva, or urine.

It is another object of the invention to provide an apparatus for collecting and analyzing a fluid specimen which will reliably provide a predetermined volume of sample to a test strip.

It is a further object of the invention to provide an apparatus for collecting and analyzing a fluid specimen which can controllably provide in excess of 10 microliters of sample to the test strip.

It is also an object of the invention to provide an apparatus for collecting and analyzing a fluid specimen which is simple to manufacture and assemble.

In accord with these objects, which will be discussed in detail below, an immunoassay apparatus and kit particularly useful for diagnosing disease is provided. The immunoassay apparatus includes a barrel which defines a relatively large chamber, an open top, and a narrow passageway opposite the open top. An analytical test means (e.g., a test strip) is located in the chamber. The test means preferably includes indicator means. A sink filter or other stopper is preferably also provided in the chamber to prevent the test means from falling out of the chamber and to prevent any liquid from exiting the chamber. In a first, presently preferred embodiment of the invention, an integral frit which includes a wider splash filter and a narrow wick portion is provided. The frit is inserted into the chamber through its wide open end, and is located such that the splash filter portion of the frit sits in the bottom of the chamber and the wick extends through and preferably out of the narrow passageway tube. The frit is formed from a polyester, polyethylene, or other material which is preferably relatively hard and molded, and at least a portion of the wick and preferably the entire wick is treated with a wetting agent to make the wick hydrophilic. If desired, a portion of the splash filter adjacent the wick may also be treated with a wetting agent. At least a portion of the splash filter adjacent the test strip remains hydrophobic. Thus, by controlling the amount of wetting agent applied to different portions of the frit, the amount of liquid sample that the wick (and where applicable the splash filter) will absorb may be carefully controlled.

In a second embodiment of the invention, instead of the frit, a separate splash filter and wick are provided. The wick is shaped to have a bulbous end portion and a narrower long portion which is located in the narrow passageway tube. At least a portion of the wick and preferably the entire wick is treated with a wetting agent to make the wick hydrophilic. The splash filter is preferably hydrophobic. The volume of the bulbous portion of the wick is used to control the absorptive capacity of the device.

According to the invention, a kit includes either of the embodiments of the immunoassay apparatus plus a buffer vial which is preferably sealed with a penetrable foil. The barrel of the immunoassay apparatus preferably fits in an air-tight manner into the vial thus inducing a pressure that flushes at least a portion of the content of the vial through the wick and the splash filter, thereby forcing the sample into contact with the test means.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1A:
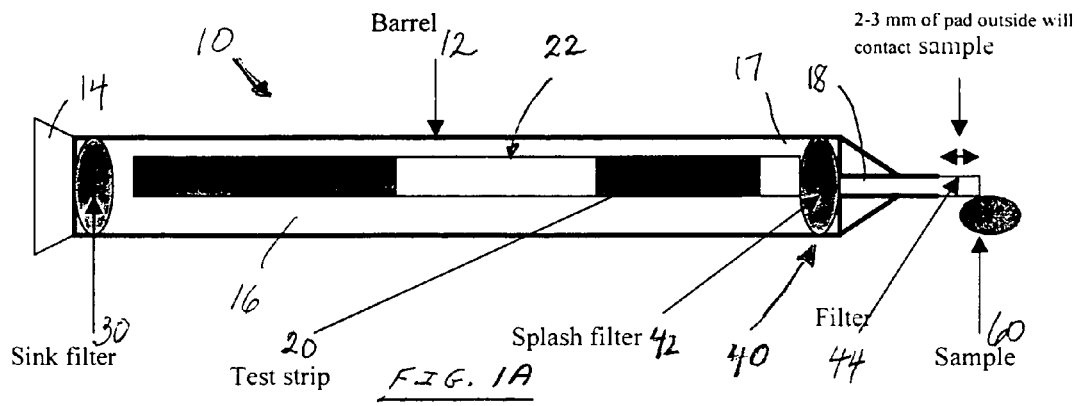
FIGS. 1a-1c are schematic diagrams showing a first embodiment of the apparatus of the invention in use.
Figure 2:
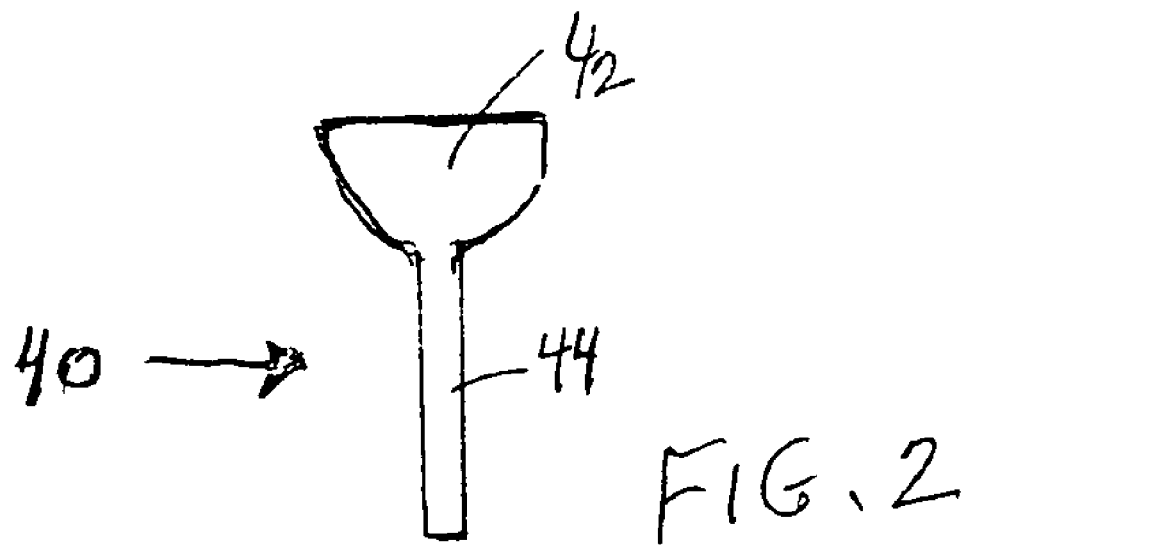
FIG. 2 is a diagram of a frit of FIGS. 1a-1c.

Turning now to FIG. 1a, a first embodiment of an immunoassay apparatus 10 is seen. Apparatus 10 includes a typically cylindrical barrel 12 formed from plastic or glass. The barrel 12 has an open end 14, and defines a chamber 16 having a second end 17, and a narrow passageway 18 extending from the second end 17 opposite the open end 14. An analytical test means 20 (e.g., a test strip) is located in the chamber 17. The test means preferably includes indicator means 22 which typically includes a diagnostic or test line 24 and a control line 26 such as disclosed in U.S. Pat. No. 5,935,864 to Schramm et al. which is hereby incorporated by reference herein in its entirety. The test means can test for HIV1 and/or HIV2 antibodies, tuberculosis, or any of many biological agents as is well known in the art. According to one aspect of the invention, a sink filter, desiccant, or other stopper element 30 is preferably also provided in the chamber 16 and performs the function of preventing the test means 20 from falling out of the chamber and preventing any liquid from exiting the chamber. In the case of a desiccant, element 30 also advantageously controls exposure of the test strip to humidity. The desiccant can take any of many forms such as silica gel or clay in tablet form or in a bag made from TYVEK, cloth, or Kraft paper, etc., and is available from Dry Pak Industries of Studio City, Calif. In addition, according to a first embodiment of the invention which is seen in FIGS. 1a and 2, an integral filter or frit 40 which includes a wider splash filter 42 integral with a narrow wick portion 44 is provided. During assembly, the frit 40 is inserted into the chamber through the wide open end 14 of the chamber, and the frit is located in the chamber 16 such that the splash filter portion 42 sits in the bottom (i.e., the second end 17) of the chamber 16 and the wick 44 extends through and preferably out (e.g., by 2 or 3 millimeters) of the narrow passageway 18. The splash filter 42 preferably covers an entire cross-sectional area of the barrel 12. The frit 40 may be retained in the apparatus by the frictional fit of the splash filter portion 42 in the second end 17 of the chamber 16, and/or by the frictional fit of the wick 44 in the narrow passageway 18, and/or by utilizing an adhesive, or by any other mechanism. The frit 40 is formed from a polyester, polyethylene, or other material which is preferably relatively hard and molded, as substantially described in U.S. Pat. No. 14,635,488 to Kremer, which is hereby incorporated by reference herein in its entirety. The hardness of the frit is preferably between 50 and 100 on the Shore A scale, and more preferably between 90 and 100 Shore A. In addition, at least a portion of the wick and preferably the entire wick is treated with a wetting agent to make the wick hydrophilic. Preferred wetting agents include FSN available from Dupont, or Triton-X100 or Tween 20 which are available from Pierce Biotechnology Inc., Rockford, Ill., although other wetting agents can be utilized which make the wick hydrophilic but which will not react with a biological sample.

According to one aspect of the invention, in addition to the wick, a portion of the splash filter 42 adjacent the wick 44 is also treated with a wetting agent while at least a portion of the splash filter adjacent the test strip 20 remains hydrophobic. Thus, by controlling parameters of wick and, where applicable the splash filter, subjected to the wetting agent, the amount of liquid sample that the wick, and where applicable the splash filter, will absorb may be carefully controlled. Thus, for example, the wick may be treated so that 10 microliters of sample will be absorbed. Or, as another example, the wick and a portion of the frit may be treated so that 20 microliters of sample will be absorbed. Or, as another example, the wick and a larger portion of the frit may be treated so that 40 microliters of sample will be absorbed.

Among the parameters which control the absorptivity of the wick and filter are the pore size and the volume of material wetted. An exemplary pore size for a polyethylene or polyester frit is 60 microns. Of course, everything else being equal, the larger the pore size, the faster the sample will be absorbed. Relatively larger pore sizes are desirable when working with viscous samples such as saliva.

An exemplary frit according to the invention will have a splash filter having a diameter of 0.228", a thickness of 0.140", and a chamfer angle of 50 degrees, and a wick having a length of 0.307" and a diameter of 0.042". The wick will extend through a narrow passageway of approximately 0.189" in length so that approximately 0.118" of the wick will extend beyond the barrel.

According to the invention, a kit of the invention includes apparatus 10 and a buffer vial 50 containing liquid buffer 52 and sealed with a foil seal (not shown) as is well known in the art.

Figure 1B:
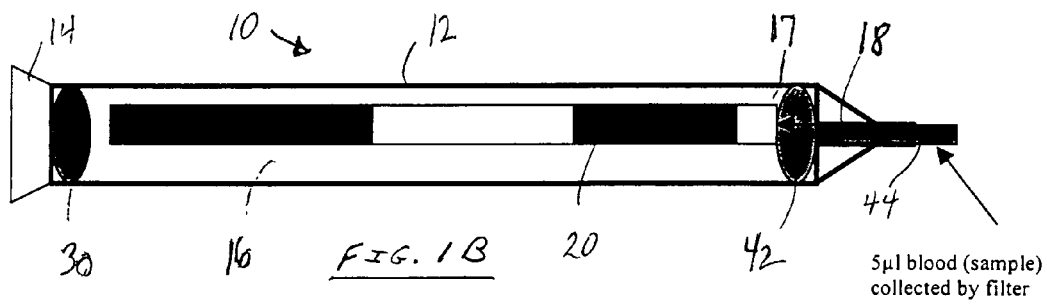
Figure 1C:
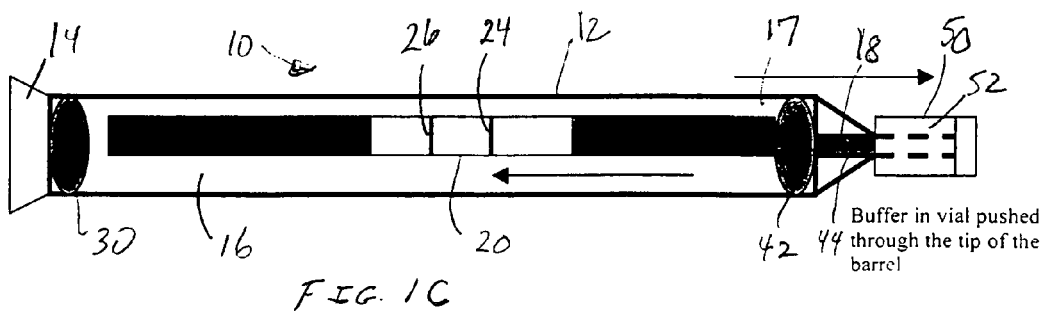

In use, and as seen in FIG. 1a, the wick 44 of the apparatus 10 is brought into contact with a sample 60. A controlled amount of the sample 60 is absorbed by the hydrophilic wick 44 of the frit (FIG. 1b) and by any treated portion of the splash filter 42. Then, as seen in FIG. 1c, the wick 44 of the apparatus 10 is pushed into the buffer vial 50, preferably in an air-tight manner such that the liquid buffer 52 is forced up the wick and pushes the sample through the hydrophobic portion of the splash filter 42 until the sample is brought into contact with the test strip 20. Since test strip 20 is absorbent, the sample is wicked up the test strip through the test area (and beyond) such that an analytical test is conducted in a manner well known in the art.

Figure 4:
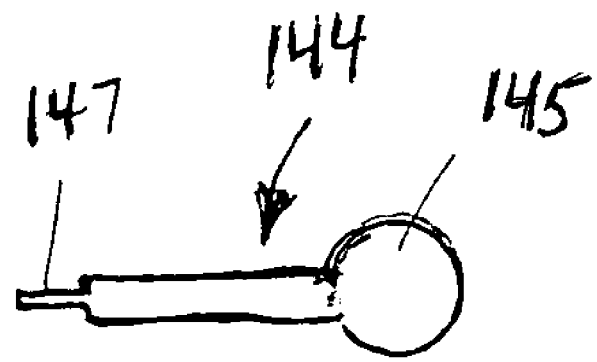
FIG. 4 is a diagram of the wick of FIGS. 3a-3c.
Figure 3A:
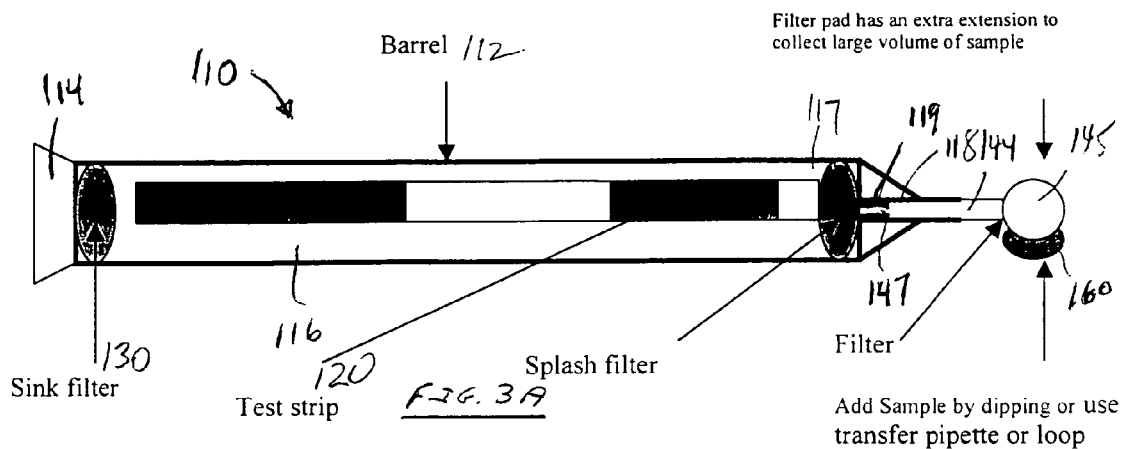
FIGS. 3a-3c are schematic diagrams showing a second embodiment of the apparatus of the invention in use.

A second embodiment of an immunoassay apparatus 110 is seen in FIG. 3a. Apparatus 110 includes a typically cylindrical barrel 112 formed from plastic or glass. The barrel 112 has an open end 114, and defines a chamber 116 having a second end 117, and a narrow passageway 118 extending from the second end 117 opposite the open end 114. The narrow passageway preferably has a stepped down portion or neck 119 adjacent the second end 117 of the chamber. An analytical test means 120 (e.g., a test strip) is located in the chamber 117. The test means preferably includes indicator means 122 which typically includes a diagnostic line 124 and a control line 126 such as disclosed in U.S. Pat. No. 5,935,864 to Schramm et al. which is hereby incorporated by reference herein in its entirety. A sink filter 130 or other stopper and a splash filter 142 are preferably also provided in the chamber 116. The sink filter prevents the test means 120 from falling out of the chamber and prevents any liquid from exiting the chamber, while the splash filter, which sits in the bottom (i.e., the second end 117) of chamber 116 and preferably covers an entire cross-sectional area of the barrel 112 prevents the sample from splashing in the chamber when it is forced into the chamber as discussed hereinafter. In addition, a wick 144 is provided with a bulbous tip portion 145 and a stepped down or tapered portion 147 (see also FIG. 4). In assembly, the wick 144 is inserted into the narrow passageway 118 from external the apparatus 110, with the stepped down portion 147 of the wick 144 engaging the neck 119 of the passageway 118, and preferably contacting the splash filter 142. The wick 144 may be retained in the apparatus by the frictional fit of the wick 144 in the narrow passageway 118, and/or by utilizing an adhesive, or by any other mechanism. The wick is formed from a polyester, polyethylene, or other material which is preferably relatively hard and molded, as substantially described in U.S. Pat. No. 4,635,488 to Kremer, which is hereby incorporated by reference herein in its entirety. In addition, at least a portion of the wick is treated with a wetting agent to make that portion of the wick hydrophilic. Preferred wetting agents include FSN available from Dupont, or Triton-X100 or Tween 20 which are available from Pierce Biotechnology Inc., Rockford, Ill., although other wetting agents can be utilized which make the wick hydrophilic but which will not react with a biological sample. According to one aspect of the invention, the entire wick is treated by wetting agents to make the wick hydrophilic. In accord with another aspect of the invention, a portion of the wick directly adjacent the splash filter is not treated. According to another aspect of the invention, the size of the bulbous portion of the wick is controlled such that the amount of liquid sample that the wick will absorb may be carefully controlled. Thus, for example, the bulbous portion of the wick may be formed so that 10 microliters of sample will be absorbed by the wick. Or, as another example, the bulbous portion of the wick may be formed so that 20 microliters of sample will be absorbed. Or, as another example, the bulbous portion of the wick may be formed so that 40 microliters of sample will be absorbed.

According to the invention, a kit of the invention includes apparatus 110 and a buffer vial 150 containing liquid buffer 152 and sealed with a foil seal (not shown) as is well known in the art.

Figure 3B:
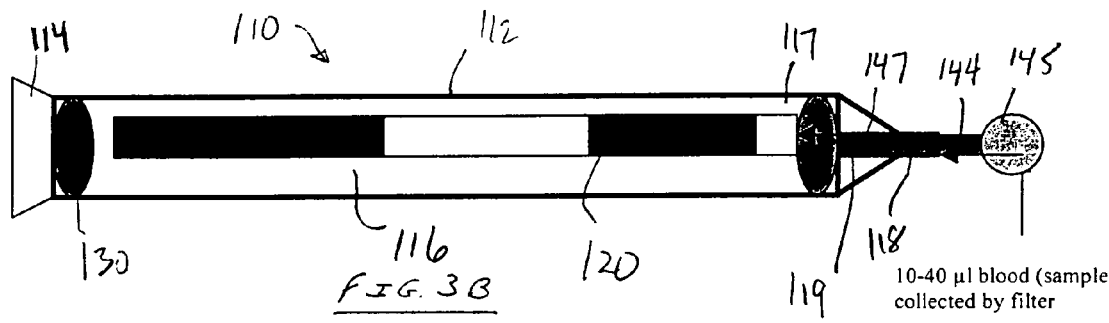
Figure 3C:
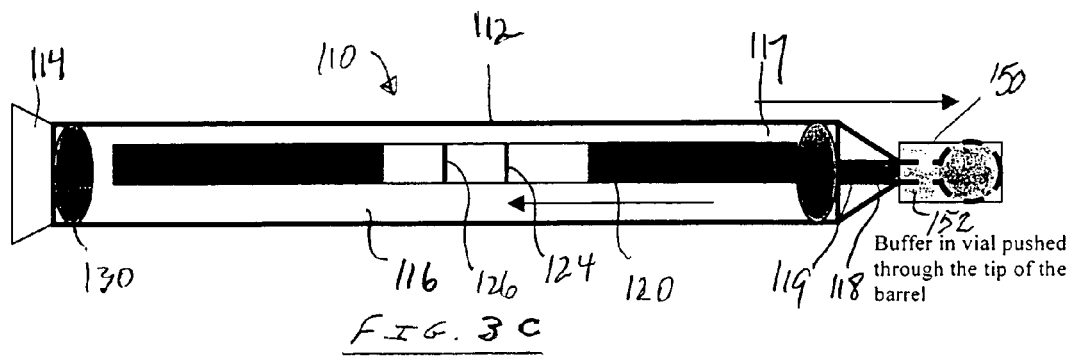

In use, and as seen in FIG. 3a, the wick bulbous tip portion 145 of the apparatus 110 is brought into contact with a sample 160. A controlled amount of the sample 160 is absorbed by the hydrophilic wick 144 (FIG. 3b). Then, as seen in FIG. 3c, the bulbous portion 145 of the wick 144 of the apparatus 110 is pushed into the buffer vial 150 preferably in an air-tight manner such that liquid buffer 152 is forced up the wick and pushes the sample through the splash filter 142 such that the sample is brought into contact with the test strip 120. Since test strip 120 is absorbent, the sample is wicked up the test strip through the test area (and beyond) such that an analytical test is conducted in a manner well known in the art.

It should be appreciated by those skilled in the art that the test means of either embodiment may be loose in the barrel or may be fixed in the barrel. If loose in the barrel, when the barrel is held vertically, the test strip contacts the splash filter in the desired configuration.

There have been described and illustrated herein embodiments of an immunoassay apparatus and kit. While particular embodiments of the invention have been described, it is not intended that the invention be limited thereto, as it is intended that the invention be as broad in scope as the art will allow and that the specification be read likewise. Thus, while in one embodiment a frit with an integral splash filter and wick was described, and in another embodiment a wick with a bulbous end was used in conjunction with a separate splash filter, it will be appreciated that in yet another embodiment, a separate splash filter and wick can be utilized without a bulbous wick end, where a portion of the separate splash filter is wetted so that the portion of the filter touching the wick is hydrophilic while the portion of the splash filter closest the test means is hydrophobic. Also, while particular materials have been disclosed for use as a wick and splash filter, other materials known in the art could be used, and while material having particular hardnesses were disclosed for the wick and splash filter, similar or other materials having different hardnesses can be utilized. Similarly, while particular wetting agents for have been disclosed, it will be appreciated that other wetting agents could be utilized as well. Also, while particular desiccants have been disclosed, others could be utilized as well. In addition, while wicks and frits which absorb particular volumes have been disclosed, it will be understood that the wicks or frits can be controlled to absorb different volumes of sample. In fact, via simple experimentation, different fixed volumes of wetting agents can be applied to identical wicks or frits which are then measured for their absorbency. Then, in the manufacturing procedure, identical wicks or frits can be generated, but different sample capacity systems can be generated by controlling the volume of wetting agent applied to the wick or frit. Moreover, while particular configurations have been disclosed in reference to a test means it will be appreciated that other configurations could be used as well. It will therefore be appreciated by those skilled in the art that yet other modifications could be made to the provided invention without deviating from its spirit and scope as claimed.

What is claimed is:

1. A biological sampling apparatus, comprising:
   a barrel defining a chamber having a first end and a narrow passageway at a second end opposite the first end;
   an absorbent analytical test means located in the chamber; and
   a frit having a first portion acting as a splash filter and located in said chamber, and a second portion integral with said first portion acting as a wick, said second portion extending through said narrow passageway, at least a portion of said splash filter being hydrophobic, and at least a portion of said wick being treated with a wetting agent to be hydrophilic.

2. An apparatus according to claim 1, wherein:
said first end of said barrel is substantially open.

3. An apparatus according to claim 2, further comprising:
a sink filter located between said test means and said first end of said barrel.

4. An apparatus according to claim 3, wherein:
said sink filter is comprises a desiccant.

5. An apparatus according to claim 1, wherein:
said entire wick and at least a portion of said splash filter are treated with a wetting agent to be hydrophilic.

6. An apparatus according to claim 5, wherein:
said entire wick and said portion of said splash filter treated with a wetting agent provide a predetermined quantitative sample absorptivity.

7. An apparatus according to claim 1, wherein:
said frit comprises at least one of polyester and polyethylene.

8. An apparatus according to claim 7, wherein:
said frit is a molded frit.

9. An apparatus according to claim 1, wherein:
said wick extends beyond said barrel.

10. An apparatus according to claim 1, wherein:
said chamber has a cross-sectional area at said second end, and said splash filter covers said cross-sectional area.

11. An apparatus according to claim 1, wherein:
said frit is friction fit in said barrel.

12. An apparatus according to claim 1, wherein:
said test means includes a test line sensitive to at least one of HIV1 antibodies, HIV2 antibodies, and tuberculosis antibodies, and a control line.

13. A biological sampling kit, comprising: said biological sampling apparatus of claim 1, and a separate vial containing buffer solution.

14. A biological sampling apparatus, comprising:
a barrel defining a chamber having a first end and a narrow passageway at a second end opposite the first end;
an absorbent analytical test means located in the chamber; and
a hydrophobic splash filter located in said chamber adjacent said narrow passageway; and
a hydrophilic wick having a first portion located in said narrow passageway and a second portion located outside said passageway and outside said barrel, said second portion having a bulbous portion capable of absorbing substantially more fluid sample than said first portion.

15. An apparatus according to claim 14, wherein:
said first end of said barrel is substantially open.

16. An apparatus according to claim 14, wherein:
said test means includes a test line sensitive to at least one of HIV1 antibodies, HIV2 antibodies, and tuberculosis antibodies, and a control line.

17. An apparatus according to claim 14, wherein:
said wick comprises at least one of polyester and polyethylene.

18. An apparatus according to claim 17, wherein:
said wick is a molded wick.

19. An apparatus according to claim 14, further comprising:
a sink filter comprising a desiccant located between said test means and said first end of said barrel.

20. A biological sampling kit comprising said biological sampling apparatus of claim 14, and a separate vial containing buffer solution.

21. A biological sampling apparatus, comprising:
a barrel defining a chamber having a first end and a narrow passageway at a second end opposite the first end;
an absorbent analytical test means located in the chamber;
a hydrophilic wick extending through said narrow passageway; and
an integral splash filter located in said chamber and in contact with said hydrophilic wick, wherein a first portion of said integral splash filter adjacent said wick is hydrophilic, and a second portion of said integral splash filter closest said test means is hydrophobic.

22. A biological sampling apparatus according to claim 21, wherein:
said wick is made hydrophilic with a wetting agent.

* * * * *